United States Patent
McEwen et al.

(10) Patent No.: US 11,723,670 B2
(45) Date of Patent: Aug. 15, 2023

(54) AUTOMATIC TOURNIQUET APPARATUS HAVING PATIENT HAZARD SHIELD

(71) Applicant: Western Clinical Engineering Ltd., Vancouver (CA)

(72) Inventors: James Allen McEwen, Vancouver (CA); Michael Jameson, North Vancouver (CA); Tom Yu Chia Lai, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 172 days.

(21) Appl. No.: 17/203,630

(22) Filed: Mar. 16, 2021

(65) Prior Publication Data

US 2022/0296252 A1    Sep. 22, 2022

(51) Int. Cl.
    *A61B 17/135* (2006.01)
    *A61B 90/00* (2016.01)
    *A61B 17/00* (2006.01)

(52) U.S. Cl.
    CPC .......... *A61B 17/1355* (2013.01); *A61B 90/06* (2016.02); *A61B 2017/00022* (2013.01); *A61B 2017/00119* (2013.01); *A61B 2017/00199* (2013.01); *A61B 2090/065* (2016.02)

(58) Field of Classification Search
    CPC .............. A61B 17/132; A61B 17/1322; A61B 17/1325; A61B 17/135; A61B 17/1355; A61B 90/06; A61B 2090/065; A61B 2017/00022; A61B 2017/00119; A61B 2017/00199; A61B 5/022; A61B 5/02233; A61H 9/005; A61H 9/0078
    See application file for complete search history.

(56) References Cited

U.S. PATENT DOCUMENTS

| 4,469,099 A | 9/1984 | McEwen |
| 4,479,494 A | 10/1984 | McEwen |
| 4,548,198 A | 10/1985 | Manes |
| 5,439,477 A | 8/1995 | McEwen |
| 5,556,415 A | 9/1996 | McEwen et al. |

(Continued)

OTHER PUBLICATIONS

International Search Report and Written Opinion for PCT/IB2022/052390, dated May 31, 2022.

*Primary Examiner* — Timothy J Neal
*Assistant Examiner* — James R McGinnity
(74) *Attorney, Agent, or Firm* — Klarquist Sparkman, LLP

(57) ABSTRACT

An automatic tourniquet apparatus comprises a tourniquet cuff, a pressure transducer, a user interface, a patient hazard shield and a pressure regulator. The pressure transducer produces a cuff pressure signal. The user interface produces a reference pressure signal. The patient hazard shield is responsive to the cuff pressure signal and the reference pressure signal, and operable during a regulation time period to produce a patient hazard signal if, in one implementation, a current level of pressure in the tourniquet cuff is greater than the reference level of pressure by at least a predetermined overpressure limit. The pressure regulator is responsive to the patient hazard signal, and has a pressurizing element for increasing pressure in the cuff and a depressurizing element for decreasing pressure in the cuff. The pressurizing element is configured to be non-responsive if the patient hazard signal is produced.

17 Claims, 2 Drawing Sheets

(56) References Cited

U.S. PATENT DOCUMENTS

| | | |
|---|---|---|
| 5,607,447 A | 3/1997 | McEwen et al. |
| 5,855,589 A | 1/1999 | McEwen et al. |
| 5,931,853 A | 8/1999 | McEwen et al. |
| 6,213,939 B1 | 4/2001 | McEwen |
| 2010/0211096 A1* | 8/2010 | McEwen ............ A61B 17/1355 606/202 |

* cited by examiner

AUTOMATIC TOURNIQUET APPARATUS HAVING PATIENT HAZARD SHIELD

BACKGROUND

Automatic tourniquet systems are commonly used in surgery to occlude the flow of arterial blood into a portion of a patient's limb, thus creating a clear, dry surgical field that facilitates the performance of a surgical procedure and improves outcomes. A typical automatic tourniquet system of the prior art includes a tourniquet cuff for encircling a patient's limb at a desired location, a tourniquet instrument, and flexible tubing connecting the cuff to the instrument. The tourniquet instrument includes a pressure regulator operable during a regulation time period for automatically controlling the pressure in the cuff near a reference pressure desired by the user. The pressure regulator consists of a pressurizing element that responds to a pressurizing signal to increase the level of pressure in the cuff. The pressure regulator also consists of a depressurizing element that responds to a depressurizing signal to decrease the level of pressure in the cuff. Many types of such pneumatic surgical tourniquet systems have been described in the prior art, such as those described by McEwen in U.S. Pat. Nos. 4,469,099, 4,479,494, 5,439,477 and by McEwen and Jameson in U.S. Pat. Nos. 5,556,415 and 5,855,589.

McEwen in U.S. Pat. No. 4,469,099 described an automatic tourniquet system that triggers audiovisual alarms to alert the user of potential problems such as when cuff pressure exceeds or falls below the reference pressure by more than 15 mmHg. Manes in U.S. Pat. No. 4,548,198 described automatic tourniquet apparatus having a manually adjustable overpressure valve which limits the maximum pressure delivered to the cuff in the event a malfunction of the apparatus. A major limitation of Manes'198 is that the overpressure valve must be set either manually in relation to different reference pressures desired by a user, a labor-intensive and error-prone technique, or must be set at a hazardously high fixed pressure well above normally safe reference pressure settings. Further, Manes'198 could not be modified to provide an underpressure valve to safely limit the minimum pressure in the cuff in the event of a malfunction of the apparatus.

McEwen in U.S. Pat. No. 5,931,853 described a physiologic tourniquet using a digital processor for pressure regulation and having a safety circuit which detects certain types of malfunctions involving undesired valve actuations for different modes of operation (cuff modes). Two major limitations of the safety circuit of the prior art limit its ability to shield a patient from clinically significant malfunctions. First, the safety circuit of the prior art does not monitor cuff pressure to identify hazardous differences between a desired reference pressure and the actual cuff pressure. Second, the safety circuit of the prior art requires the mode of operation of the cuff and the states of the pressurizing and depressurizing elements. Thus, the safety circuit of the prior art cannot detect possible malfunctions of the processor, its embedded software, or valves employed as pressurizing elements and depressurizing elements. More specifically, in McEwen'853, possible cuff modes are 'cuff inflating', 'cuff deflation', and 'cuff regulating'. McEwen'853 has a list of predetermined set of undesired valve actuations for each cuff mode. If the safety circuit detects any one of the undesired valve actuations specific to the current cuff mode, then it immediately disconnects the supply of electrical power to all valves. However, McEwen'853 requires a cuff mode output signal from the processor to determine whether an undesired valve actuation has occurred. Thus, if the processor malfunctions, or a software error occurs, an incorrect cuff mode signal may be received by the safety circuit resulting in false positive, or false negative triggers. Another limitation to the safety circuit of the prior art is that upon detection of an undesired valve actuation, electrical power to the valves is interrupted immediately, rendering the tourniquet apparatus non-functional for the duration of a surgical procedure.

SUMMARY

The foregoing and other objects, features, and advantages of the invention will become more apparent from the following detailed description, which proceeds with reference to the accompanying figures.

In some implementations, an automatic tourniquet apparatus comprise a tourniquet cuff, a pressure transducer adapted to produce a cuff pressure signal indicative of a level of pressure in the tourniquet cuff, a user interface adapted to produce a reference pressure signal indicative of a reference level of pressure in the tourniquet cuff desired by a user, a patient hazard shield responsive to the cuff pressure signal and the reference pressure signal and operable during a regulation time period to produce a patient hazard signal if a current level of pressure in the tourniquet cuff is greater than the reference level of pressure by at least a predetermined overpressure limit, and a pressure regulator responsive to the patient hazard signal and having a pressurizing element responsive to a pressurizing signal for increasing pressure in the tourniquet cuff and further having a depressurizing element responsive to a depressurizing signal for decreasing pressure in the tourniquet cuff. The pressure regulator is operable during the regulation time period for regulating pressure in the cuff near the desired reference level of pressure by selectively producing the pressurizing signal and the depressurizing signal. The pressurizing element is configured to be non-responsive to the pressurizing signal if the patient hazard signal is produced.

The pressurizing element can be further configured to be non-responsive to the pressurizing signal after a predetermined hazard period if the patient hazard signal is detected at an end of the predetermined hazard period. The depressurizing element can be adapted to be non-responsive to the depressurizing signal if the patient hazard signal is detected at the end of the predetermined hazard period.

The predetermined overpressure limit can be set at a level that may be indicative of a malfunction of the pressure regulator. In some implementations, the predetermined overpressure limit is set at 50 mmHg.

The user interface can be adapted to enable the user to select the predetermined overpressure limit from a plurality of overpressure limits.

The predetermined hazard period can be a function of the predetermined response time of the pressure regulator. In some implementations, the predetermined hazard period is 200 ms.

In some implementations, an indication that the patient hazard signal has been produced is stored in a non-volatile memory of the patient hazard shield, and the user interface is adapted to prevent initiation of a regulation time period if the stored indication is present in the non-volatile memory.

In some implementations, an automatic tourniquet apparatus comprises a tourniquet cuff, an automatic tourniquet instrument having a pressure transducer adapted to produce a cuff pressure signal indicative of a level of pressure in the tourniquet cuff, a user interface adapted to produce a reference pressure signal indicative of a reference level of pressure in the tourniquet cuff desired by a user, a pressure regulator responsive to the reference pressure signal and further responsive to the cuff pressure signal, wherein the pressure regulator is operable during a regulation time period for maintaining pressure in the tourniquet cuff near the reference level of pressure, and a patient hazard shield responsive to the cuff pressure signal and the reference pressure signal. The patient hazard shield is operable to produce a patient hazard alert if pressure in the tourniquet cuff differs from the reference level of pressure by at least a predetermined pressure difference and is operable independently of the pressure regulator during the regulation time period.

In some implementations, an automatic tourniquet apparatus comprises a tourniquet cuff, a pressure transducer adapted to produce an indication of a level of pressure in the tourniquet cuff, a pressure regulator operable during a regulation time period for regulating the level of pressure in the tourniquet cuff near a reference pressure level, and a patient hazard shield operable during the regulation time period for producing a patient hazard alert if the level of pressure in the tourniquet cuff is at least equal to an overpressure limit. The pressurizing element of the pressure regulator is rendered inoperable when the patient hazard alert is produced.

The overpressure limit can be set to correspond to a level of pressure that may be indicative of a malfunction of the pressure regulator. In some implementations, the overpressure limit is 450 mmHg.

The overpressure limit can be set to correspond to a level of pressure greater than the reference pressure level by an amount that may be indicative of a malfunction of the pressure regulator. In some implementations, the overpressure limit is 50 mmHg.

In some implementations, the pressure regulator can be rendered inoperable after the end of a predetermined hazard period if the patient hazard alert is detected at the end of the predetermined hazard period.

In some implementations, the predetermined hazard period is a function of the predetermined response time of the pressure regulator.

In some implementations, an indication that the patient hazard alert has been produced is stored in a non-volatile memory of the patient hazard shield, and a user interface connected to the automatic tourniquet apparatus is configured to prevent initiation of a regulation time period if the stored indication is present in the non-volatile memory.

According to a method implementation, a method of producing a patient hazard alert in an automatic tourniquet apparatus comprises providing a tourniquet cuff, providing an automatic tourniquet instrument having a pressure transducer adapted to produce a cuff pressure signal indicative of a level of pressure in the tourniquet cuff, a user interface adapted to produce a reference pressure signal indicative of a reference level of pressure in the tourniquet cuff desired by a user, and a pressure regulator responsive to the reference pressure signal and the cuff pressure signal, providing a patient hazard shield responsive to the cuff pressure signal and the reference pressure signal, operating the pressure regulator to maintain pressure in the tourniquet cuff near the reference level of pressure during a regulation time period, operating the patient hazard shield independently of the pressure regulator during the regulation time period, wherein the patient hazard shield produces a patient hazard alert if pressure in the tourniquet cuff differs from the reference level of pressure by at least a predetermined pressure difference.

The predetermined pressure difference can be determined from the pressure in the tourniquet cuff compared to at least one of a predetermined overpressure limit and a predetermined underpressure limit.

DETAILED DESCRIPTION

Figure 1:
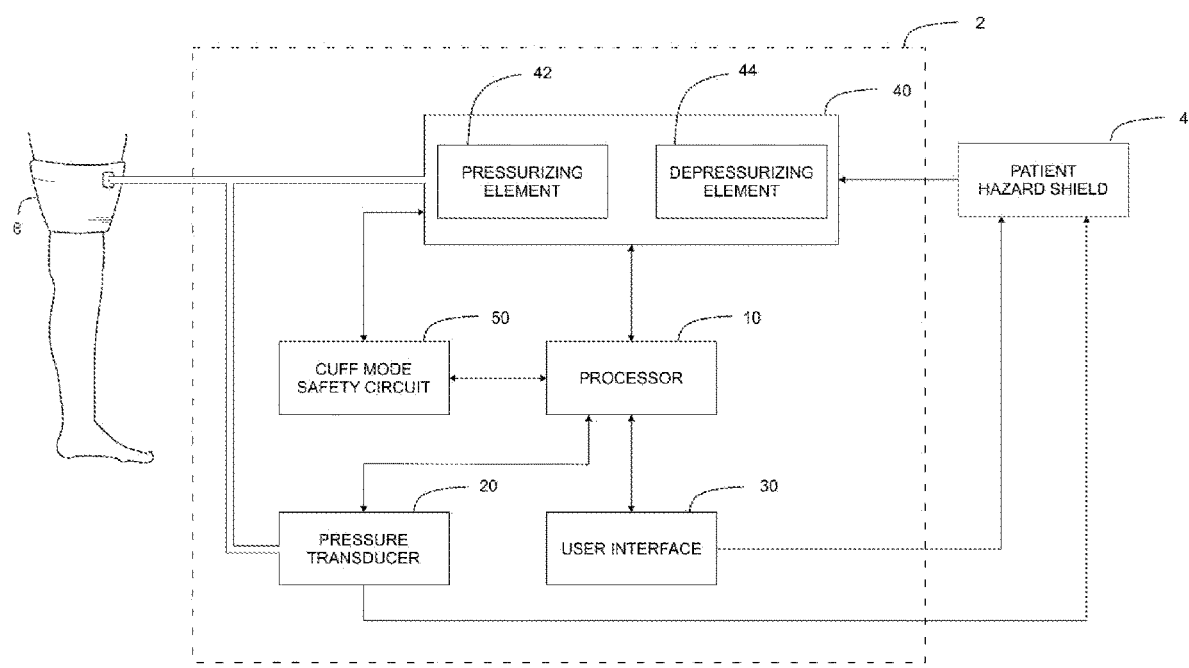
FIG. 1 is a block diagram of a patient hazard shield as configured for operation with an automatic tourniquet apparatus.

FIG. 1 depicts a block diagram of a preferred embodiment of automatic tourniquet apparatus 2 having a patient hazard shield 4. Tourniquet cuff 6 having an inflatable bladder is shown pneumatically connected to automatic tourniquet apparatus 2 and in place on a limb of a patient. Automatic tourniquet apparatus 2 comprises, processor 10, pressure transducer 20, user interface 30, pressure regulator 40, and cuff mode safety circuit 50.

The patient hazard shield 4 is used with automatic tourniquet apparatus 2, but operates independently thereof, as is described in further detail below. The patient hazard shield 4 is connected to the pressure regulator 40, user interface 30, and pressure transducer 20.

Processor 10 communicates with pressure transducer 20, user interface 30, pressure regulator 40, and cuff mode safety circuit 50 to control the operation of automatic tourniquet apparatus 2.

Pressure transducer 20 generates and communicates to processor 10 and to patient hazard shield 4 a cuff pressure signal which indicates the level of pressure inside tourniquet cuff 6.

User interface 30 communicates with processor 10 and patient hazard shield 4. User interface 30 may selectively display any of the following information: the level of pressure within tourniquet cuff 6 (cuff pressure); the pressure level to be maintained in tourniquet cuff 6 when tourniquet cuff 6 is inflated (reference pressure); the length of time that tourniquet cuff 6 has been inflated (regulation time period); inflation time alarm limit; alarm messages describing detected alarm events; and other information pertinent to the operation of automatic tourniquet apparatus 2. User interface 30 includes controls for the user to adjust the reference pressure, or inflation time alarm limit; inflate, or deflate tourniquet cuff 6, to start or end the regulation time period, respectively; and other controls pertinent to the operation of automatic tourniquet apparatus 2. The regulation time period begins when the user initiates an inflation of tourniquet cuff 6 through user interface 30. The regulation time period ends when the level of pressure in tourniquet cuff 6 is deflated to a pressure near 0 mmHg. User interface 30 may include an audio transducer and visual indicators to produce audiovisual alarms to the user during various alarm conditions such as when the regulation time period exceeds the inflation alarm time limit. In the preferred embodiments, user interface 30 is an LCD graphical display with integrated touch screen, an LED indicator and an audio transducer, but it will be appreciated that other types of user interfaces capable of receiving user input and communicating information may be used.

Pressure regulator 40 is pneumatically connected to tourniquet cuff 6 and communicates with processor 10 to regulate the pressure inside pressure tourniquet cuff 6 near the reference pressure during the regulation time period. Pressure regulator 40 includes pressurizing element 42 and depressurizing element 44. Pressurizing element 42 responds to a pressurizing signal to increase the level of pressure in tourniquet cuff 6. Depressurizing element 44 responds to a depressurizing signal to decrease the level of pressure in tourniquet cuff 6. In the preferred embodiment, pressure regulator 40 generates the pressurizing signal and depressurizing signal based on the cuff pressure signal, and the reference pressure signal indicative of the desired level of pressure in tourniquet cuff 6. However, it will be apparent to a person skilled in the art that pressure regulator 40 may include a pressure transducer for generating the cuff pressure signal. It will also be apparent to a person skilled in the art that processor 10 may generate and communicate the pressurizing signal and depressurizing signal to pressure regulator 40.

Cuff mode safety circuit 50 communicates with processor 10 and pressure regulator 40 to monitor and detect undesired combination of activation of pressurizing element 42 and depressurizing element 44 and cuff mode. Cuff mode safety circuit 50 is described in McEwen U.S. Pat. No. 5,931,853, which is incorporated herein by reference.

Patient hazard shield 4 communicates with pressure transducer 20, user interface 30, and pressure regulator 40 to monitor cuff pressure to identify hazardous differences between the reference pressure and the actual cuff pressure. Patient hazard shield 4 is independent of the regulation of the level of pressure inside tourniquet cuff 6 by processor 10 and pressure regulator 40. Patient hazard shield 4 does not require any information from processor 10 or pressure regulator 40 to function, allowing patient hazard shield 4 to shield a patient encircled by tourniquet cuff 6 from malfunctions in processor 10 and/or pressure regulator 40 that caused hazardous differences between the reference pressure and the actual cuff pressure.

In some implementations, at least part of patient hazard shield 4 is an electrical circuit independently operable from the processor 10, the pressure regulator 40, the cuff mode safety circuit 50 and the pressure transducer 20. In some implementations, the patient hazard shield 4 is implemented as a separate circuit component from processor 10, pressure regulator 40, cuff mode safety circuit 50 and pressure transducer 20. In other implementations, patient hazard shield 4 may be implemented in one or more distinct areas on the same circuit component(s) as the processor 10, the pressure regulator 40, the cuff mode safety circuit 50 and the pressure transducer 20.

Figure 2:
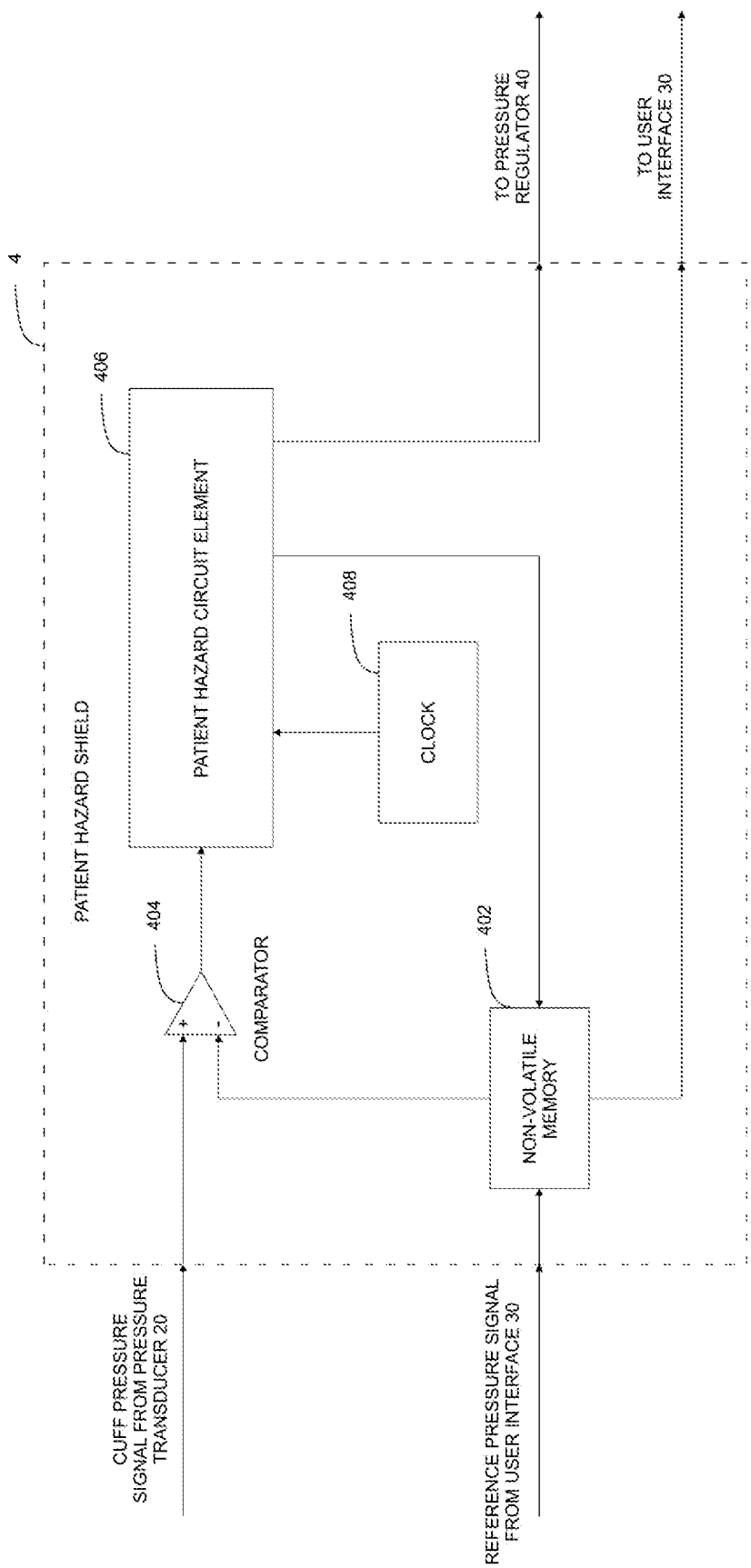
FIG. 2 is a block diagram of the patient hazard shield of FIG. 1.

FIG. 2 depicts a block diagram of patient hazard shield 4. Patient hazard shield 4 comprises a non-volatile memory 402, a comparator 404, a patient hazard circuit element 406, and a clock 408.

Non-volatile memory 402 generates an overpressure limit signal based on a reference pressure signal received from user interface 30. The overpressure limit signal is indicative of an overpressure limit which is a level of pressure that is deemed to be undesirable, hazardous and/or indicative of a malfunction of pressure regulator 40 if the cuff pressure exceeds it. The overpressure limit may be a predetermined pressure value above the reference pressure, such as 50 mmHg above the reference pressure. Alternatively, the overpressure limit may be a predetermined pressure value minus the reference pressure, such as 450 mmHg minus the reference pressure (i.e. the overpressure limit is 450 mmHg). Alternatively, the overpressure limit may be selected by the user from a plurality of overpressure limits through user interface 30. It will be apparent to a person skilled in the art that the overpressure limit may change depending on the reference pressure. For example, if the reference pressure is below 400 mmHg, the overpressure limit is 450 mmHg, and if the reference pressure is above 400 mmHg, the overpressure limit is 650 mmHg.

The overpressure limit signal from the non-volatile memory 402 and the cuff pressure signal from pressure transducer 20 are compared by the comparator 404 and the result is communicated to the patient hazard circuit element 406. The patient hazard circuit element 406 produces a patient hazard signal indicative of a patient hazard alert if the cuff pressure signal is greater than the overpressure limit signal (i.e., cuff pressure is greater than overpressure limit), and communicates the pressure hazard signal to pressure regulator 40. In response to the patient hazard signal, the pressurizing element 42 is adapted to be non-responsive to the pressurizing signal, thereby preventing pressure regulator 40 from inadvertently increasing the cuff pressure further, and only allowing pressure regulator 40 to attempt to decrease the level of pressure in tourniquet cuff 6 below the overpressure limit by the activation of depressurizing element 44.

When the cuff pressure signal is greater than the overpressure limit signal, the patient hazard circuit element 406 may also start a timer for a hazard period through clock 408. If the patient hazard signal is present at the end of the hazard period, the potential problem is confirmed and pressurizing element 42 and depressurizing element 44 are adapted to be non-responsive to the pressurizing signal and the depressurizing signal, respectively, resulting in pressure regulator 40 becoming inoperable, thereby keeping the level of pressure inside tourniquet cuff 6 stable. The hazard period is a predetermined time period sufficiently long for the pressure regulator 40, under normal operation, to correct a potential problem and regulate cuff pressure to be below the overpressure limit through depressurizing element 44. In the preferred embodiment, the predetermined time period is 200 ms (milliseconds), or based on a response time of the pressure regulator 40. The response time of the pressure regulator 40 is a predetermined, and measurable duration of time for pressure regulator 40 to regulate the level of pressure inside tourniquet cuff 6 from a first reference pressure to a second reference pressure. In the preferred embodiment, the response time is determined by measuring the time required for pressure regulator 40 to regulate cuff pressure from a first reference pressure of 300 mmHg to a second reference pressure of 250 mmHg. It will be apparent to a person skilled in the art that the response time may be measured from an alternative first reference pressure and an alternative second reference pressure.

If the patient hazard signal continues to be present after the hazard time period, patient hazard circuit element 406 may store an indication that a hazard has occurred in the non-volatile memory 402. Patient hazard shield 4 communicates an indication that a hazard has occurred to user interface 30. In response, user interface 30 may be adapted to prevent the user from initiating a regulation time period. During servicing, the stored indication can be cleared from non-volatile memory 402.

In some implementations, the patient hazard shield comprises a CCLD (complex programmable logic device) configured to have a first input, a second input, the memory, the comparator and the outputs as described above in connection with FIG. 2. Other devices, such as FPGAs, could also be used.

An example of the implementation of the preferred embodiment is described below.

a.) Tourniquet cuff 6 is applied to a patient for a surgical procedure by a user. User interacts with user interface 30 to set the reference pressure desired in tourniquet cuff 6 to 300 mmHg thereby inflating tourniquet cuff 6 and starting a regulation time period.

b.) Pressure regulator 40 produces pressurizing signal to pressurizing element 42 to increase the level of pressure in tourniquet cuff 6 to the reference pressure. Pressure regulator proceeds to regulate the level of pressure in tourniquet cuff 6 near the reference pressure for the duration of the surgical procedure through pressurizing element 42 and depressurizing element 44.

c.) During the surgical procedure, the cuff pressure exceeds an overpressure limit of reference pressure plus 50 mmHg due to limb manipulation typically experienced during surgery. Patient hazard shield 4 generates a patient hazard signal, starts a timer for a hazard period of 200 ms, and communicates to pressure regulator 40 to make pressurizing element 42 non-responsive to the pressurizing signal, thereby preventing pressure regulator 40 from inadvertently increasing the level of pressure in cuff 6 further In this example, pressure regulator 40 is able to correct the potential problem and regulate cuff pressure to be below the overpressure limit through depressurizing element 44. As such, the patient hazard signal is no longer produced by patient hazard shield 4 and automatic tourniquet apparatus 2 remains functional.

d.) At a different instance in time during the surgical procedure, an electrical fault internal to automatic tourniquet apparatus 2 causes the pressurizing element 42 to activate undesirably. As a result, the level of pressure inside tourniquet cuff 6 gradually increases to a level above the overpressure limit of 350 mmHg again (reference pressure plus 50 mmHg). Patient hazard shield 4 generates a patient hazard signal, starts a timer for a hazard period of 200 ms, and communicates to pressure regulator 40 to make pressurizing element 42 non-responsive to the pressurizing signal. Because the pressurizing element has a hardware malfunction, pressure regulator 40 is unable to bring the pressure level in tourniquet cuff 6 to fall below the overpressure limit within the hazard period of 200 ms. As result, patient hazard shield 4 confirms the hazardous overpressure condition, identifies that a malfunction has occurred, and therefore communicates to pressure regulator 40 to make pressurizing element 42 and depressurizing element 44 non-responsive to pressurizing signal and depressurizing signal, respectively, resulting in pressure regulator 40 becoming inoperable thereby keeping the level of pressure inside tourniquet cuff 6 stable. Patient hazard shield 4 successfully identifies a malfunction that cuff mode safety circuit 50, of the prior art described by McEwen'853, would not be able to identify since the activation of pressurizing element 42 is permitted during the regulation cuff mode as described by McEwen'853.

e.) Patient hazard shield 4 communicates to and stores in non-volatile memory an indication that the patient hazard signal has been produced for a period of time longer than the hazard time period. The stored indication is communicated to user interface 30 to prevent future initiation of a regulation time period by the user, thereby preventing automatic tourniquet apparatus 2 to be used while the malfunction has been detected. In this example, user interface 30 produces an alert to user when subsequent inflation of a tourniquet cuff is attempted. The alert may notify the user that a malfunction has been detected in the past and that automatic tourniquet apparatus 4 should be serviced.

f.) After service by trained personnel, the stored indication can be cleared from non-volatile memory 402 to allow user to initiate a regulation time period through user interface 30.

Instead of monitoring and responding to hazardous overpressure conditions as described above, it will be appreciated that patient hazard shield 4 may monitor hazardous underpressure conditions. As such, non-volatile memory 402 generates an underpressure limit signal based on the reference pressure signal from user interface 30. The underpressure limit signal is indicative of an underpressure limit which is a level of pressure that is deemed to be undesirable, hazardous and indicative of a malfunction of pressure regulator 40 if cuff pressure falls below it. The underpressure limit may be a predetermined pressure value below the reference pressure, such as 50 mmHg below the reference pressure. Alternatively, the underpressure limit may be selected by the user from a plurality of underpressure limits through user interface 30. It will be apparent to a person skilled in the art that the underpressure limit may change depending on the reference pressure.

The underpressure limit signal from non-volatile memory 402 and the cuff pressure signal from pressure transducer 20 are compared by comparator 404 and the result is communicated to patient hazard circuit element 406. Patient hazard circuit element 406 produces and communicates to pressure regulator 40 a patient hazard signal indicative of a patient hazard alert if the cuff pressure signal is less than the underpressure limit signal (i.e., cuff pressure is less than underpressure limit). In response to the patient hazard signal, depressurizing element 44 is adapted to be non-responsive to the depressurizing signal thereby preventing pressure regulator 40 from inadvertently decreasing the cuff pressure further and only allowing pressure regulator 40 to attempt to increase the level of pressure in tourniquet cuff 6 above the underpressure limit by the activation of pressurizing element 42.

When the cuff pressure signal is less than the underpressure limit signal, patient hazard circuit element 406 may also start a timer for a hazard period through clock 408. If the patient hazard signal is present at the end of the hazard period, the potential problem is confirmed and pressurizing element 42 and depressurizing element 44 are adapted to be non-responsive to the pressurizing signal and depressurizing signal, respectively, resulting in pressure regulator 40 becoming inoperable thereby keeping the level of pressure inside tourniquet cuff 6 stable. The hazard period is a predetermined time period sufficiently long for the pressure regulator 40, under normal operation, to correct a potential problem and regulate cuff pressure to be above the underpressure limit through pressurizing element 42. The predetermined time period may be 200 ms, or based on a response time of pressure regulator 40. Response time of pressure regulator 40 is a predetermined, and measurable duration of time for pressure regulator 40 to regulate the level of pressure inside tourniquet cuff 6 from a first reference pressure to a second reference pressure. In the preferred embodiment, the response time is determined by measuring the time required for pressure regulator 40 to regulate cuff pressure from a first reference pressure of 250 mmHg to a second reference pressure of 300 mmHg. It will be apparent to a person skilled in the art that the response time may be measured from alternative first reference pressure and alternative second reference pressure.

It will be apparent to a person skilled in the art that patient hazard shield 4 may compare the cuff pressure to both an overpressure limit and an underpressure limit to generate a patient hazard signal.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An automatic tourniquet apparatus, comprising:
a tourniquet cuff;
a pressure transducer adapted to produce a cuff pressure signal indicative of a level of pressure in the tourniquet cuff;
a user interface adapted to produce a reference pressure signal indicative of a reference level of pressure in the tourniquet cuff desired by a user;
a patient hazard shield responsive to the cuff pressure signal and the reference pressure signal and operable during a regulation time period to produce a patient hazard signal if a current level of pressure in the tourniquet cuff is greater than the reference level of pressure by at least a predetermined overpressure limit; and
a pressure regulator responsive to the patient hazard signal and having a pressurizing element responsive to a pressurizing signal for increasing pressure in the tourniquet cuff and further having a depressurizing element responsive to a depressurizing signal for decreasing pressure in the tourniquet cuff;
wherein the pressure regulator is operable during the regulation time period for regulating pressure in the cuff near the desired reference level of pressure by selectively producing the pressurizing signal and the depressurizing signal; and
wherein the pressurizing element is configured to be non-responsive to the pressurizing signal if the patient hazard signal is produced.

2. The automatic tourniquet apparatus of claim 1, wherein the pressurizing element is further configured to be non-responsive to the pressurizing signal after a predetermined hazard period if the patient hazard signal is detected at an end of the predetermined hazard period, and wherein the depressurizing element is adapted to be non-responsive to the depressurizing signal if the patient hazard signal is detected at the end of the predetermined hazard period.

3. The automatic tourniquet apparatus of claim 2, wherein the predetermined hazard period is a function of the predetermined response time of the pressure regulator.

4. The automatic tourniquet apparatus of claim 3, wherein the predetermined hazard period is 200 ms.

5. The automatic tourniquet apparatus of claim 1, wherein the predetermined overpressure limit is set at a level that may be indicative of a malfunction of the pressure regulator.

6. The automatic tourniquet apparatus of claim 5, wherein the predetermined overpressure limit is set at 50 mmHg.

7. The automatic tourniquet apparatus of claim 1, wherein the user interface is further adapted to enable the user to select the predetermined overpressure limit from a plurality of overpressure limits.

8. The automatic tourniquet apparatus of claim 1, wherein an indication that the patient hazard signal has been produced is stored in a non-volatile memory of the patient hazard shield, and wherein the user interface is adapted to prevent initiation of a regulation time period if the stored indication is present in the non-volatile memory.

9. An automatic tourniquet apparatus, comprising:
a tourniquet cuff;
an automatic tourniquet instrument having
a pressure transducer adapted to produce a cuff pressure signal indicative of a level of pressure in the tourniquet cuff;
a user interface adapted to produce a reference pressure signal indicative of a reference level of pressure in the tourniquet cuff desired by a user; and
a pressure regulator responsive to the reference pressure signal and further responsive to the cuff pressure signal, wherein the pressure regulator is operable during a regulation time period for maintaining pressure in the tourniquet cuff near the reference level of pressure; and
a patient hazard shield responsive to the cuff pressure signal and the reference pressure signal, wherein the patient hazard shield is operable to produce a patient hazard signal if pressure in the tourniquet cuff differs from the reference level of pressure by at least a predetermined pressure difference; and
wherein the pressure regulator is rendered inoperable during the regulation time period if the patient hazard signal is produced.

10. An automatic tourniquet apparatus, comprising:
a tourniquet cuff;
a pressure transducer adapted to produce an indication of a level of pressure in the tourniquet cuff;
a pressure regulator operable during a regulation time period for regulating the level of pressure in the tourniquet cuff near a reference pressure level; and
a patient hazard shield operable during the regulation time period for producing a patient hazard alert if the level of pressure in the tourniquet cuff is at least equal to an overpressure limit,
wherein a pressurizing element of the pressure regulator is rendered inoperable when the patient hazard alert is produced.

11. The automatic tourniquet apparatus of claim 10, wherein the overpressure limit corresponds to a level of pressure that may be indicative of a malfunction of the pressure regulator.

12. The automatic tourniquet apparatus of claim 11, wherein the overpressure limit is 450 mmHg.

13. The automatic tourniquet apparatus of claim 10, wherein the overpressure limit corresponds to a level of pressure greater than the reference pressure level by an amount that may be indicative of a malfunction of the pressure regulator.

14. The automatic tourniquet apparatus of claim 13, wherein the overpressure limit is 50 mmHg.

15. The automatic tourniquet apparatus of claim 10, further characterized by rendering the pressure regulator to be inoperable after the end of a predetermined hazard period if the patient hazard alert is detected at the end of the predetermined hazard period.

16. The automatic tourniquet apparatus of claim 15, wherein the predetermined hazard period is a function of the predetermined response time of the pressure regulator.

17. The automatic tourniquet apparatus of claim 10, wherein an indication that the patient hazard alert has been produced is stored in a non-volatile memory of the patient hazard shield, and wherein a user interface connected to the automatic tourniquet apparatus is configured to prevent initiation of a regulation time period if the stored indication is present in the non-volatile memory.

* * * * *